United States Patent
Huysmans et al.

(10) Patent No.: US 10,481,587 B2
(45) Date of Patent: Nov. 19, 2019

(54) ORTHOSIS

(71) Applicants: Universiteit Antwerpen, Antwerp (BE); VZW More Institute, Deurne (BE)

(72) Inventors: Toon Huysmans, Rotterdam (NL); Jan Jozef Maria Sijbers, Duffel (BE); Frederik Verstreken, Schoten (BE)

(73) Assignees: Universiteit Antwerpen, Antwerp (BE); VZW More Institute, Deurne (BE)

( * ) Notice: Subject to any disclaimer, the term of this patent is extended or adjusted under 35 U.S.C. 154(b) by 68 days.

(21) Appl. No.: 15/572,328

(22) PCT Filed: May 9, 2016

(86) PCT No.: PCT/IB2016/052628
§ 371 (c)(1),
(2) Date: Nov. 7, 2017

(87) PCT Pub. No.: WO2016/181282
PCT Pub. Date: Nov. 17, 2016

(65) Prior Publication Data
US 2018/0113438 A1    Apr. 26, 2018

(30) Foreign Application Priority Data
May 13, 2015    (BE) .................................... 20155299

(51) Int. Cl.
*A61F 5/01*    (2006.01)
*G05B 19/4099*    (2006.01)
(Continued)

(52) U.S. Cl.
CPC ........ *G05B 19/4099* (2013.01); *A61B 5/1077* (2013.01); *A61F 5/01* (2013.01);
(Continued)

(58) Field of Classification Search
CPC ........ A61F 5/01; A61F 5/0111; A61F 5/0118; A61F 5/013; A61F 5/02
See application file for complete search history.

(56) References Cited

U.S. PATENT DOCUMENTS 8,055,046 B2 * 11/2011 Feilkas .................... G06T 7/50
                                                            345/420
8,838,263 B2    9/2014 Sivak et al.
(Continued)

FOREIGN PATENT DOCUMENTS

EP    0636354 A1    2/1995
GB    2508204 A    5/2014

*Primary Examiner* — Vincent H Tran
(74) *Attorney, Agent, or Firm* — Rudy J. Ng; Bret E. Field; Bozicevic, Field & Francis LLP

(57) ABSTRACT

Method for making an orthosis of a body part of a person, wherein the method comprises of: —measuring the body part with a shape and in a pose in order to obtain measurement data of the body part; —correlating the measurement data of the body part to a predetermined statistical shape model of a corresponding reference body part in order to calculate parameters of the statistical shape model; —digitally forming an orthosis model on the basis of the statistical shape model with the known parameters; —producing the orthosis via a CAD/CAM system on the basis of the digitally formed orthosis model.

10 Claims, 2 Drawing Sheets

(51) Int. Cl.
*A61F 5/02* (2006.01)
*B33Y 80/00* (2015.01)
*A61B 5/107* (2006.01)
*B33Y 50/00* (2015.01)
*G16H 50/50* (2018.01)

(52) U.S. Cl.
CPC ............ *A61F 5/013* (2013.01); *A61F 5/0111* (2013.01); *A61F 5/0118* (2013.01); *A61F 5/02* (2013.01); *B33Y 50/00* (2014.12); *B33Y 80/00* (2014.12); *G16H 50/50* (2018.01); *A61B 5/1079* (2013.01); *A61F 5/0106* (2013.01); *G05B 2219/49023* (2013.01)

(56) References Cited

U.S. PATENT DOCUMENTS

| | | | | |
|---|---|---|---|---|
| 2004/0133431 | A1* | 7/2004 | Udiljak | A43B 7/141 |
| | | | | 705/26.1 |
| 2009/0306801 | A1* | 12/2009 | Sivak | A61F 5/0111 |
| | | | | 700/98 |
| 2010/0268135 | A1 | 10/2010 | Summit et al. | |
| 2012/0265496 | A1* | 10/2012 | Mahfouz | A61B 17/14 |
| | | | | 703/1 |
| 2013/0166256 | A1* | 6/2013 | Wirx-Speetjens | G06F 17/50 |
| | | | | 703/1 |
| 2013/0271458 | A1* | 10/2013 | Andriluka | G06K 9/00342 |
| | | | | 345/420 |
| 2014/0067107 | A1* | 3/2014 | Stanhope | G01B 5/008 |
| | | | | 700/98 |
| 2014/0142486 | A1* | 5/2014 | Summit | A61F 5/05841 |
| | | | | 602/20 |
| 2015/0117728 | A1* | 4/2015 | Choi | G06K 9/6201 |
| | | | | 382/128 |
| 2016/0331463 | A1* | 11/2016 | Notzli | G06T 19/20 |
| 2017/0027477 | A1* | 2/2017 | Charles | A61B 5/1036 |

* cited by examiner

ORTHOSIS

The invention relates to a method for making an orthosis for a body part of a person.

An orthosis is an externally worn aid which can for instance be used to correct positional deviations or abnormal mobility of joints or of the spinal column. An orthosis can typically fulfil two different functions, i.e. a relieving/supporting function and a corrective function. Examples of orthoses are a knee brace, ankle brace, a wrist brace, an elbow brace or back orthosis. In order to be able to fulfil their functions, such orthoses are typically made to measure in order to at least partially enclose a predetermined body part of a person in a specific pose. Because the shape of a body part differs from person to person, and because the specific pose in which the body part is enclosed by the orthosis depends on the objective of the orthosis, each orthosis is preferably unique.

An example of a traditional manner of making an orthosis comprises of a doctor or a medical orthopaedic expert bringing the body part of the person into the correct pose and then arranging a plaster material or alternative plastic material around the body part, wherein the plaster material or plastic material hardens at least partially, such that a cast of the body part in the specific pose is obtained. This cast then forms the basis for production of the orthosis. This traditional method is labour-intensive and prone to errors in that different factors in the process of making the cast can have a negative effect on the accuracy of the cast.

Ideas have been proposed of providing 3-D scanners for measuring the body part in a specific pose, such that an orthosis can be made on the basis of the 3-D scan. 3-D scanners which are accurate enough for the scan to be used as basis for forming an orthosis are however found to be very expensive in practice.

US2014/0067107 describes a method and system for generating prostheses and orthoses. A digital model, parameterized at least for characterizing clinical shapes and characteristics of the device, is provided here with a plurality of design parameter values and 3-D coordinates of captured and calculated virtual landmarks in order to construct a customized unique model corresponding to the specifications. A drawback of this method and this system is that the digital model is directly related to the prostheses and orthoses. More specifically, predetermined landmarks on the body part must be measured, which are then related to points on the model of the orthosis. This limits the freedom of forming of the orthosis and increases the error-proneness.

It is an object of the present invention to provide an alternative method for making an orthosis of a body part of a person.

The invention provides for this purpose a method for making an orthosis of a body part of a person, wherein the method comprises of:
  measuring the body part with a shape and in a pose in order to obtain measurement data of the body part;
  correlating the measurement data of the body part to a predetermined statistical shape model of a corresponding reference body part in order to calculate parameters of the statistical shape model;
  digitally forming an orthosis model on the basis of the statistical shape model with the known parameters;
  producing the orthosis via a CAD/CAM system on the basis of the digitally formed orthosis model.

In the method according to the invention the body part is on the one hand measured with a shape and in a pose. A predetermined statistical shape model of a corresponding reference body part is on the other hand available. The measurement data are then correlated to the statistical shape model in order to calculate parameters thereof. The orthosis is then formed and produced on the basis of the statistical shape model with the parameters. It will be apparent here that the step of correlating the measurement data of the body part to the predetermined statistical shape model has for its object to give the statistical shape model, which has the property of changing shape and pose when parameters are changed, substantially the same shape and pose as the measured body part. This makes it possible to still form an accurate orthosis model on the basis of measurement data with a relatively limited accuracy and/or resolution. This is because the orthosis model is formed on the basis of the statistical shape model after calculation of the parameters for giving the statistical shape model the same shape and pose as the measured body part. This makes it possible to still produce an accurate, correct and high-quality orthosis with relatively simple measuring equipment or scanning equipment.

The method according to the invention provides a separation between measuring and mapping of the shape of the body part on the one hand and forming of the orthosis on the other. By first measuring and correlating to a statistical shape model, a complete 3-D model of the body part with high accuracy can be obtained on the basis of an inexpensive measurement and/or measurement with inferior accuracy and/or incomplete measurement owing to the correlation to the shape model. In contrast to the prior art, where landmarks need typically be marked on the body part of the patient, which is very prone to error, landmarks can in the method of the invention be incorporated into the shape model. An orthosis with high accuracy can hereby be designed and with almost endless design freedom.

The method according to the invention allows the orthoses to be designed in advance on the basis of the shape model, wherein the designer has insight into the average shape but also the variations in shape during the design process and can use this information in order to make the orthosis design as robust as possible. The orthosis is then calculated for a patient by means of the correspondence between the shape model and the patient scan so as to connect perfectly to the geometry of the patient. The design logic of the orthosis is therefore preferably determined wholly on the basis of the shape model, while the final shape of the orthosis is determined on the basis of the patient geometry. This accelerates the designing of an orthosis considerably, without affecting the accuracy.

The method preferably further comprises the following steps of:
  selecting a plurality of reference persons, such that the shape of the reference body part of multiple reference persons differs;
  making a plurality of digital scans of the reference body part for each of the plurality of reference persons, wherein the reference body part is placed in multiple predetermined poses for making multiple ones of the plurality of digital scans;
  constructing a statistical shape model on the basis of the digital scans.

The statistical shape model for a body part is in practice typically constructed only once. The statistical shape model is constructed on the basis of a plurality of scans of the body part of a plurality of persons and in a plurality of poses, which are then referred to as reference body parts. A plurality of scans is thus obtained, wherein the shape and/or pose of the body part differs in each scan. A so-called statistical shape model can be constructed on the basis of this plurality of scans. These statistical shape models have the feature that multiple poses and/or shapes are dynamically incorporated in the model in such a way that the shape and/or pose of the model can be changed by adjusting the parameters of the statistical model. It may be useful here to store the shape and the pose in separate models. The models can then be applied in succession, the parameter set then being the combination of the parameters of the individual models. A statistical shape model could in this way be combined with a mathematical pose model, wherein this latter is for instance based on computer animation techniques. This has the advantage that it is not necessary to scan numerous poses, but only a wide set of shapes. Statistical shape models are known, and will therefore not be technically explained further in this description. By making use of the statistical shape model constructed on the basis of a plurality of reference persons a population-based aspect, which is not mentioned at any point in the prior art, is introduced in the invention. This has advantages such as generics, namely; once the patient has been defined from a shape perspective it is possible to construct any parametric orthosis on the basis thereof. Because the shape model provides the patient scan with anatomical information, the personalization can take place automatically. A further advantage is that a high-quality shape model can be constructed via low-quality scans.

The digital scans preferably have a resolution and/or accuracy which is considerably greater than the resolution and/or accuracy of the measurement data. This allows a plurality of scans of a plurality of reference persons to be made once only and at a predetermined location, where a high-accuracy scanning apparatus is available, in order to construct the statistical shape model. It is further possible to measure persons requiring an orthosis in situ and by means of a relatively inexpensive measuring device in order to collect measurement data, which are then correlated to the statistical shape model. This method of operation has multiple advantages. The basis on which the orthosis is formed is on the one hand the statistical shape model, which is formed on the basis of high-resolution scans, such that an accurate 3-D model is available for forming the orthosis. It will on the other hand not be necessary to have a relatively expensive scanner in situ each time a person needs an orthosis. This is because the body part of the person can be measured with a lower accuracy and/or resolution, without this having direct adverse effects on the forming of the orthosis. This makes it possible to measure the body part with the shape and pose of the person in simple and inexpensive manner and to still obtain on the basis of these measurement data a detailed 3-D model based on the statistical shape model in order to make the orthosis.

The statistical shape model is further preferably provided with predetermined anatomical and/or biomechanical zones to which predetermined orthosis properties have been allocated, chosen from: high stiffness, low stiffness, ventilation and reduced pressure, such that during the step of digitally forming an orthosis model the predetermined orthosis properties are applied at the position of corresponding zones of the statistical shape model. The step of forming the orthosis model is in this way simplified considerably by adding information to the statistical shape model which is related to the orthosis.

The CAD/CAM system is preferably a 3-D printer. A 3-D printer is known to be highly suitable for producing free and complex shapes.

The measuring of the body part preferably comprises of taking a plurality of photos of the body part, wherein the plurality of photos comprise predetermined sides of the body part. These photos can then be correlated to the statistical shape model on the basis of mathematical algorithms and filters. The measuring can take place by means of an inexpensive scanner, digital photos or an X-ray recorded image. A tape measure can alternatively be used to take simple 1-D measurements such as lengths, circumferences and so on, which can be related to the shape model.

The body part is preferably chosen from wrist, elbow, ankle, knee and back. Tests have shown that forming an orthosis for these body parts is typically difficult and complex, and that the method according to the invention is highly suitable for optimization of forming of an orthosis for wrist, elbow, ankle, knee or back.

The statistical shape model preferably comprises a plurality of rotation axes which are related to predetermined anatomical and/or biomechanical features of the reference body part. These rotation axes can then further be used in the determining of the parameters, particularly to define the pose of the body part of the statistical shape model.

The step of measuring the body part preferably further comprises of marking predetermined anatomical points, such that the measurement data comprise information about the location of the predetermined anatomical points, and wherein the statistical shape model further comprises reference information about the location of predetermined anatomical points on the reference body part. By marking points on the measured body part and correlating these points to predetermined reference information in the shape model it is technically considerably simpler to correlate the measurement data to the shape model. Incorrect correlations are further minimized in that anatomical points are predefined.

The invention further relates to a system for making an orthosis of a body part of a person, wherein the system comprises:
  a first measuring device for measuring the body part with a shape and in a pose in order to obtain measurement data of the body part;
  a digital processing unit for correlating the measurement data of the body part to a predetermined statistical shape model of a corresponding reference body part in order to calculate parameters of the statistical shape model;
  a digital forming unit for digitally forming an orthosis model on the basis of the statistical shape model with the calculated parameters;
  a CAD/CAM system for producing the orthosis on the basis of the digitally formed orthosis model.

The system according to the invention allows application of the method according to the invention. Effects and advantages which are described above in the context of the method will therefore also apply to the system.

The predetermined statistical shape model is preferably formed by selecting a plurality of reference persons such that the shape of the reference body part of multiple reference persons differs and by making a plurality of digital scans of the reference body part for each of the plurality of reference persons, wherein the reference body part is placed in multiple predetermined poses for making multiple ones of the plurality of digital scans, and constructing a statistical shape model on the basis of the digital scans, wherein the first measuring device has a resolution and/or accuracy which is considerably smaller than the resolution and/or accuracy of a second measuring device with which the plurality of digital scans of the reference body part were made. The first measuring device is thereby relatively simple and inexpensive, so that the threshold for measuring of the body part of the person in situ is low.

The invention will now be further described on the basis of an exemplary embodiment shown in the drawing.

In the drawing.

The same or similar elements are designated in the drawing with the same reference numeral.

The present invention originates from the search by the inventors for a solution for manufacturing braces or orthoses for wrists. The example of a brace for a wrist will therefore each time be used in the further description. It will however be apparent that the same technology can be applied to the production of other orthoses for knee, ankle, elbow, back and other body parts. Despite dealing specifically with the manufacture of an orthosis for a wrist, the description hereinbelow will therefore also contain a technical basis for application of an analog method and an analog system in analog manner for producing an orthosis for a body part other than the wrist.

Figure 1:
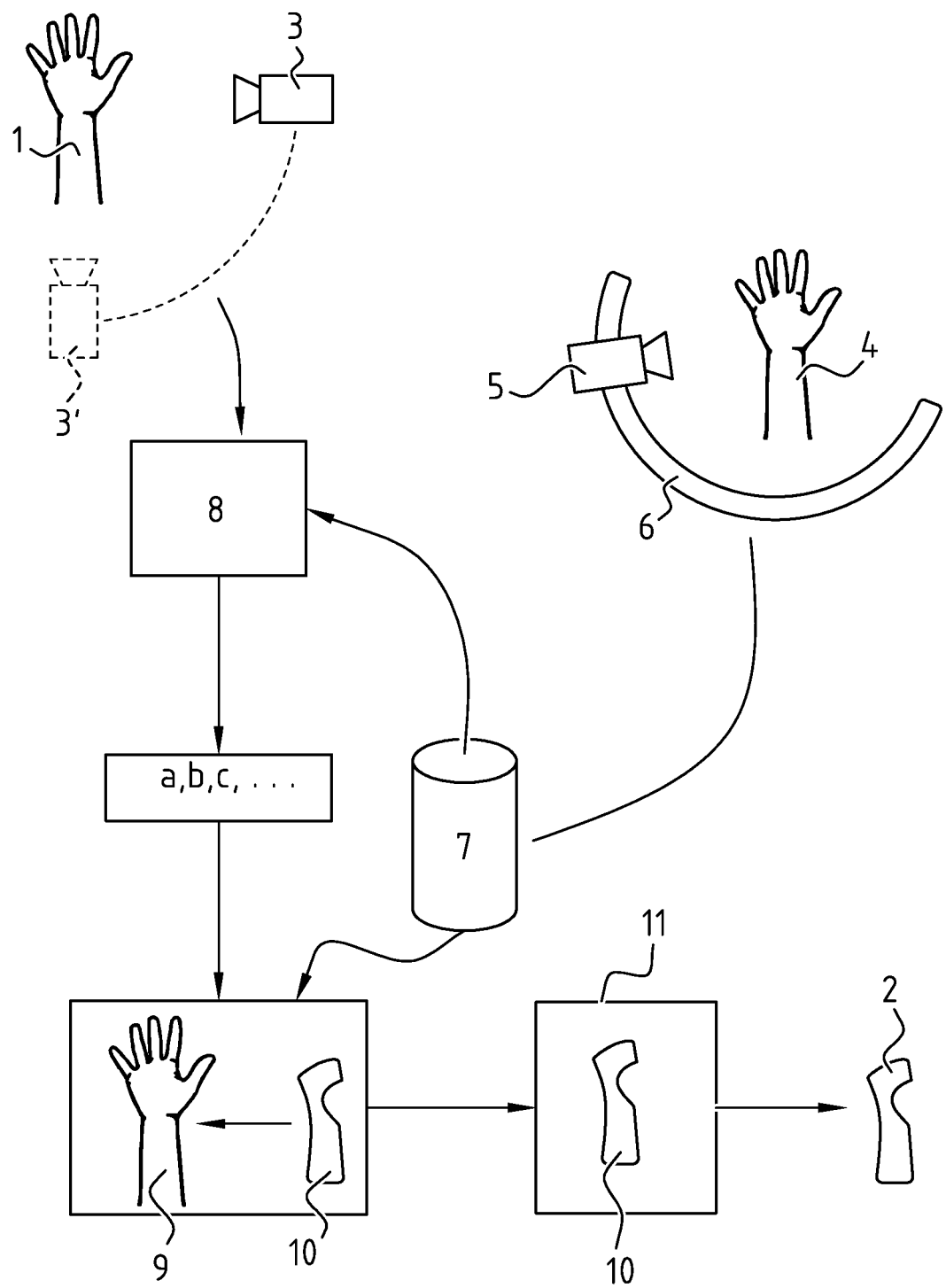
FIG. 1 shows an illustration of the system and the method according to an embodiment of the invention.

FIG. 1 illustrates the system and the method for making an orthosis according to the invention. According to the invention, an orthosis 2 is made to measure for a body part such as a wrist 1. Brace 2 here has for its object to fix and/or support wrist 1, with its specific shape, in a predetermined pose. It will be apparent here that multiple wrists of multiple persons typically also have different shapes. The term 'shape' will be defined here as a representation independent of pose which is characterized by the fixed bone structure, inter alia length of the bones, and distribution of soft tissue such as muscle and fat over the fixed bone structure. If an orthosis has to fit closely to a wrist, the specific shape of the wrist will therefore have to be taken into account. Depending on the objective of the orthosis, the wrist will also have to be fixed in a predetermined pose. An example of a predetermined pose is the pose in which all joints are in neutral position.

For specific purposes it may however also be necessary to support a wrist, wherein the wrist joint lies at a determined angle relative to the neutral position. This is typically determined by the doctor or surgeon prescribing the orthosis as treatment means.

Wrist 1 of the person for whom an orthosis is made, particularly the shape and the pose of wrist 1, is measured by means of a first measuring device 3. An example of a first measuring device 3 is a camera. The rest is preferably measured here such that information is available about a plurality of views of the wrist. If first measuring device 3 is embodied as a camera, a plurality of photos is typically taken of wrist 1 from a plurality of sides. This is illustrated schematically in FIG. 1 by showing the first measuring device 3 in multiple positions 3, 3'. The first measuring device can alternatively be a 3-D camera, such as a time-of-flight camera. The first measuring device 3 in any case has the result that measurement data of wrist 1 are collected, particularly of the shape and pose of wrist 1. In the case of the camera these measurement data are typically a plurality of images, wherein each image comprises an array of pixels. These measurement data can further be used in process step 8, which is further elucidated hereinbelow.

FIG. 1 further shows a reference wrist 4. Reference wrist 4 is scanned in high resolution and with high accuracy by a scanner 5, 6. The scanner typically comprises here a camera 5 which can record a plurality of views of the reference wrist in controlled manner. This is for instance possible by placing camera 5 on a rail system 6, as illustrated in FIG. 1. The scanner can alternatively be provided with a plurality of cameras 5 (not shown) which are placed in predetermined positions relative to the reference wrist in order to thus be able to record a digital 3-D model of the wrist with high accuracy. Such high-resolution scanners are expensive. Such scanners 5, 6 are therefore preferably not used each time a wrist 1 of a person has to be scanned. According to the invention, a plurality of reference wrists 4 of multiple persons are scanned. Each wrist has a unique shape here. Each wrist is further preferably scanned in a plurality of different positions, such that a 3-D model is available in high resolution, for different shapes of wrists and in different poses. These 3-D models are used as input for building a database 7, as further elucidated hereinbelow, such that the relatively expensive 3-D scanner for scanning the reference body parts need only be used once (once for each shape and pose), and not each time a wrist 1 has to be measured. The expensive scanner could also be a CT or MRI scanner for some applications. It will be apparent to the skilled person that the shape model can not only take on the poses and shapes present in the database as reference measurement, but that other shapes and poses can also be generated by interpolation and extrapolation.

Tests have shown that, particularly in generating of 3-D models for wrists, correctly measuring the skin surfaces of the fingers, particularly the surfaces-between adjacent fingers, is particularly complex. When forming a brace, correct information about these surfaces is important here in order to enable a comfortable brace to be made. These surfaces can be measured accurately for each of the reference wrists and in each of the poses by making use of 3-D scanners 5, 6 with high resolution. The 3-D models generated by high-resolution scanner 5, 6 on the basis of reference wrists 4 comprise accurate and correct information about the shape of outer surfaces of the wrist and of adjacent body parts such as forearm and fingers.

A statistical shape model is generated on the basis of the multiple 3-D models of reference wrists 4, which 3-D models are measured by high-resolution scanner 5, 6. A statistical shape model is also referred to as an active shape model. Statistical shape models are known and are constructed on the basis of so-called training models. The 3-D models of reference wrists 4 form the multiple training models for constructing the statistical shape model. A plurality of wrists is preferably scanned here, each with their shape V1, V2, V3, ..., Vn. A scan is more preferably made for each of the wrists V1, V2, V3, Vn in predetermined poses P1, P2, P3, ..., Pm. A total of n×m training models will thus form the basis for constructing the statistical shape model.

Constructing statistical shape models is known and is described in WO 2010/142624 of Toon Huysmans and Jan Sijbers and in for instance the document titled "Automatic construction of correspondences for tubular surfaces" by Toon Huysmans, Jan Sijbers and Brigitte Verdonk. This document is included in this description by way of reference for the purpose of explaining the technical operation of the construction of shape models. In conclusion, it can be stated that the multiple 3-D training models are placed in a combined reference coordinate system in order to construct the statistical shape model. The objective of a statistical shape model is here to mark the presence of a shape in the multiple sets of surfaces with a probability-presence function. A distribution is assumed here which is symmetric around its mean, for instance via a Gaussian distribution. The construction of a statistical shape model on the basis of a plurality of training models is known and is therefore not elucidated in further detail in this description. The statistical shape model is designated schematically in FIG. 1 with reference numeral 7.

The measurement data of first measuring device 3 of the wrist 1 of the person are correlated to the statistical shape model 7. This correlating is shown in the figure with numeral 8. Correlating is defined here as calculating parameters of statistical shape model 7, such that the statistical shape model with the calculated parameters takes on the same shape and pose as wrist 1. This is possible by applying known mathematical algorithms. An example of such a calculation is described in the publication titled 'Correspondence preserving elastic surface registration with shape model prior' by F. Danckaers, T. Huysmans, D. Laco, A. Ledda, S. Verwulgen, S. Van Dongen and J. Sijbers. While WO2010/142624 calculates parameters relative to a cylindrical surface, in the present invention parameters will be calculated relative to the statistical shape model 7. This document is included in this description by way of reference for the purpose of explaining the technical operation of the correlating and calculating of parameters a, b, c, . . . . The step of the correlating can be performed in different ways, depending on the content of the first measurement results of first measuring device 3 and depending on the manner in which statistical shape model 7 has been constructed. Different techniques for correlation are however known, and this is therefore not further explained in this description.

Figure 2:
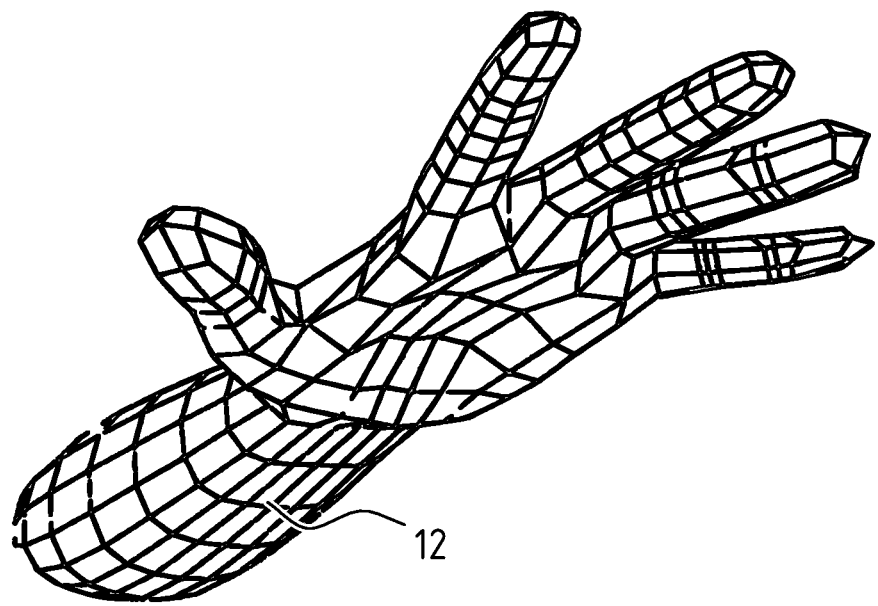
FIG. 2 shows a 3-D model of a body part of a person.

By applying the calculated parameters a, b, c, . . . to the statistical shape model a 3-D model 12 is obtained, as shown in FIG. 2. This 3-D model 12 has the same shape and pose as the wrist 1 captured by first measuring device 3. The same shape and pose is defined here as a shape and pose of the 3-D model having a predetermined maximum deviation from the shape and pose of wrist 1. 3-D model 12 further has a high information density, i.e. a high accuracy and/or a high resolution, because the 3-D model is obtained on the basis of statistical shape model 7, which was constructed on the basis of high-resolution scans of reference wrists 4. This 3-D model 12 is shown in FIG. 1 as wrist 9, on the basis of which a digital orthosis 10 can be formed. Forming of the digital orthosis can be done manually, by an orthosis designer, can be done automatically on the basis of rules added to the statistical shape model 7 and/or to orthosis design software, or can be brought about by a combination of predetermined rules/software and an orthosis designer. Because digital orthosis 10 is designed on the basis of a 3-D model 9 with a shape and in a pose equal to those of wrist 1 of the person, the orthosis is unique and is specifically adapted to the needs of the person for fulfilling their function. As further alternative, orthosis 10 can be designed on the basis of the statistical shape model 7, wherein an average shape and pose are set. Variations in shape and pose can preferably be taken into account here during the design process. When a body part of the patient is scanned, the orthosis can then be recalculated automatically so as to fit maximally to the shape and pose of the patient.

The designed orthosis 10 is then sent to a CAD/CAM system 11. An example of a CAD/CAM system is a 3-D printer. An alternative example is a multi-axle milling machine. It will be apparent here that CAD/CAM system 11 need not physically be in the same location as the location where the brace is digitally designed on the basis of 3-D model 9. Nor is it necessary for measuring device 3 to be in the same location as CAD-CAM system 11 or the design system for designing digital brace 10. Different elements of the system and of the method can be carried out at different times and at different physical locations. The statistical shape model 7 can thus be constructed once only by making a plurality of high-resolution scans of reference wrists 4 at one or more predetermined locations. In further use of the method and the system according to the invention measurement data of multiple wrists 1 can be collected at different locations and at different times for the purpose of manufacturing a brace therefor. The measurement data can each time be forwarded to one or more predetermined locations where correlation 8 takes place and/or where a digital orthosis 10 can be formed on the basis of 3-D model 9. The digitally formed brace can then be forwarded to a further location, where a CAD/CAM system produces orthosis 2 on the basis of the digitally formed orthosis 10. An orthosis with high accuracy can thus be manufactured in inexpensive and efficient manner.

Figure 3:
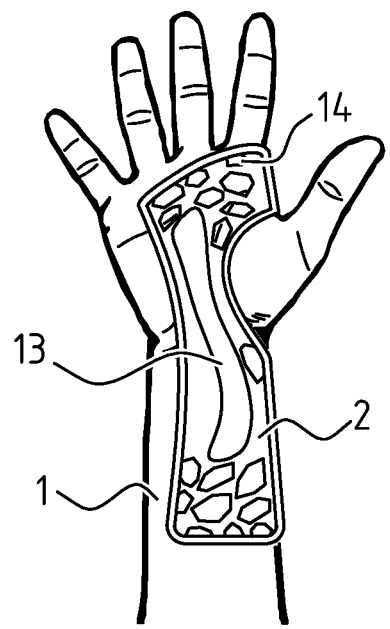
FIG. 3 shows an example of an orthosis formed by applying the system and the method of FIG. 1.

FIG. 3 shows an example of a brace 2 for a wrist 1 produced by means of 3-D printing. The brace shows a hard supporting zone 13 whereby the position of wrist 1 is fixed. The brace further shows a zone 14 in which openings are provided so that wrist 1 is minimally irritated at the position of this zone 14. This zone 14 can thus be provided with openings which allow the skin to breathe and be ventilated.

The zones of the example of FIG. 3, and further zones, can be marked on the statistical shape model and be provided with rules so that supportive and open zones of the brace can be taken into account during the design of the brace.

Anatomical reference points can further be marked on the statistical shape model. Corresponding anatomical reference points can then also be marked on the measurement results coming from first measuring device 3, so that correlating of the measurement data to the statistical shape model becomes considerably simpler.

The description and figures are intended only to illustrate the invention. It will be apparent here to the skilled person that the above described and the shown embodiments are only several possible embodiments of the invention, and that the invention can also be applied in other manner. The description and the figures are therefore not intended to limit the invention. The scope of protection will be defined solely in the claims.

The invention claimed is:

1. A method for making an orthosis of a body part of a person, the method comprising:
    measuring the body part with a shape and in a pose in order to obtain measurement data of the body part;
    correlating the measurement data of the body part to a predetermined statistical shape model of a corresponding reference body part in order to calculate parameters of the statistical shape model;
    digitally forming an orthosis model on the basis of the statistical shape model with known parameters; and
    producing the orthosis via a CAD/CAM system on the basis of the digitally formed orthosis model, and
    wherein the method is preceded by the following steps of:
    selecting a plurality of reference persons, such that a shape of the reference body part of multiple reference persons differs;
    making a plurality of digital scans of the reference body part for each of the plurality of reference persons, wherein the reference body part is placed in multiple predetermined poses for making multiple ones of the plurality of digital scans; and
    constructing a statistical shape model on the basis of the digital scans.

2. The method as claimed in claim 1, wherein the digital scans have an information density which is considerably greater than the information density of the measurement data.

3. The method as claimed in claim 1, wherein the statistical shape model is further provided with predetermined anatomical and/or biomechanical zones to which predetermined orthosis properties have been allocated, chosen from: high strength, low strength, ventilation and reduced pressure, such that during the step of digitally forming an orthosis model the predetermined orthosis properties are applied at the position of corresponding zones of the statistical shape model.

4. The method as claimed in claim 1, wherein the CAD/CAM system is a 3-D printer.

5. The method as claimed in claim 1, wherein the measuring of the body part comprises of taking a plurality of photos of the body part, wherein the plurality of photos comprise predetermined sides of the body part.

6. The method as claimed in claim 1, wherein the body part is chosen from wrist, elbow, ankle, knee and back.

7. The method as claimed in claim 1, wherein the statistical shape model comprises a plurality of rotation axes which are related to predetermined anatomical and/or biomechanical features of the reference body part.

8. The method as claimed in claim 1, wherein the step of measuring the body part further comprises of marking predetermined anatomical points, such that the measurement data comprise information about the location of the predetermined anatomical points, and wherein the statistical shape model further comprises reference information about the location of the predetermined anatomical points on the reference body part.

9. A system for making an orthosis of a body part of a person, the system comprising:
   a first measuring device for measuring the body part with a shape and in a pose in order to obtain measurement data of the body part;
   a digital processing unit for correlating the measurement data of the body part to a predetermined statistical shape model of a corresponding reference body part in order to calculate parameters of the statistical shape model;
   a digital forming unit for digitally forming an orthosis model on the basis of the statistical shape model with the calculated parameters; and
   a CAD/CAM system for producing the orthosis on the basis of the digitally formed orthosis model,
   wherein the predetermined statistical shape model is formed by selecting a plurality of reference persons such that a shape of the reference body part of multiple reference persons differs and by making a plurality of digital scans of the reference body part for each of the plurality of reference persons, wherein the reference body part is placed in multiple predetermined poses for making multiple ones of the plurality of digital scans, and constructing a statistical shape model on the basis of the digital scans, wherein the first measuring device has an information density which is considerably smaller than the information density of a second measuring device with which the plurality of digital scans of the reference body part were made.

10. The system as claimed in claim 9, wherein the CAD/CAM system is a 3-D printer.

* * * * *